United States Patent [19]

Cuscurida et al.

[11] Patent Number: 5,183,923

[45] Date of Patent: * Feb. 2, 1993

[54] PROCESS FOR PREPARING PRIMARY HYDROXYL-CONTAINING DIOLS

[75] Inventors: Michael Cuscurida; George P. Speranza, both of Austin, Tex.

[73] Assignee: Texaco Chemical Company, White Plains, N.Y.

[*] Notice: The portion of the term of this patent subsequent to Dec. 19, 2006 has been disclaimed.

[21] Appl. No.: 500,432

[22] Filed: Mar. 28, 1990

Related U.S. Application Data

[63] Continuation-in-part of Ser. No. 179,826, Apr. 11, 1988, abandoned.

[51] Int. Cl.⁵ ............................................. C07C 271/26
[52] U.S. Cl. ........................................ 560/26; 564/215; 564/474; 564/475; 564/477; 564/478; 568/606; 568/607; 568/902; 568/903
[58] Field of Search .................. 560/26; 564/215, 474, 564/475, 477, 478; 568/606, 607, 902, 903

[56] References Cited

U.S. PATENT DOCUMENTS

| 2,231,619 | 1/1966 | Speranza | 260/584 |
|---|---|---|---|
| 3,110,732 | 11/1963 | Speranza | 260/584 |
| 3,317,609 | 5/1967 | Lesesne | 260/584 |
| 3,335,186 | 8/1967 | Speranza | 260/584 |
| 3,382,284 | 5/1968 | Schulze | 260/613 |
| 3,393,243 | 7/1968 | Cuscurida | 260/615 |
| 3,535,307 | 10/1970 | Mass et al. | 260/209 |
| 3,654,370 | 4/1972 | Yeakey | 260/584 |
| 3,954,873 | 5/1976 | Gipson | 260/584 |
| 3,983,094 | 9/1976 | O'Shea | 260/77.5 |
| 4,111,924 | 9/1978 | Fujimo | 260/112.5 |
| 4,166,172 | 8/1979 | Klein | 536/4 |
| 4,228,310 | 10/1980 | Speranza et al. | 568/620 |
| 4,303,590 | 12/1981 | Tanaka et al. | 260/410.9 R |
| 4,487,853 | 12/1984 | Reichel et al. | 521/172 |
| 4,544,763 | 10/1985 | Narayan | 560/26 |
| 4,612,335 | 9/1986 | Cuscurida et al. | 521/167 |
| 4,683,279 | 7/1987 | Milligen et al. | 528/67 |
| 4,888,446 | 12/1989 | Klein et al. | 564/478 |

OTHER PUBLICATIONS

Wiley & Sons, "Protective Groups in Organic Chemistry", 1981, pp. 81–82.

Journal of Organic Chemistry, vol. 52, pp. 1881–1884, 1987, "Nafion-H Catalyzed Di-t-butylation of Aromatic Compounds".

Olah et al., J. Org. Chem., vol. 52, pp. 1881–1884, 1987.

*Primary Examiner*—Jose G. Dees
*Assistant Examiner*—Deborah D. Carr
*Attorney, Agent, or Firm*—Jack H. Park; Kenneth R. Priem

[57] ABSTRACT

The invention concerns a method for the preparation of polyurethane, polyester, polyamide, and polyurea diols which contain essentially all primary hydroxyl groups without capping by ethylene oxide. The method comprises coupling an alkylene oxide adduct of propylene glycol t-butyl ether or butylene glycol t-butyl ether or its aminated derivative with organic diisocyanates or dibasic acids followed by cleavage of the t-butyl group with an acid catalyst.

The resulting diol is useful in many types of urethane applications including foams, elastomers and coatings.

6 Claims, No Drawings

1

PROCESS FOR PREPARING PRIMARY HYDROXYL-CONTAINING DIOLS

CROSS REFERENCE

This is a continuation-in-part of application Ser. No. 07/179,826 filed Apr. 11, 1980, now abandoned.

RELATED APPLICATION

This application is related to application Ser. No. 07/179,827 and application Ser. No. 07/179,828 filed of even date.

FIELD OF THE INVENTION

This invention relates to methods for preparing primary hydroxyl-containing diols.

BACKGROUND OF THE INVENTION

Primary hydroxyl-containing diols are a desirable material for a variety of industrial uses including the manufacture of polyurethanes, polyureas, and other materials. It would be desirable to provide a facile method for manufacturing primary hydroxyl-containing diols in relatively pure form without the use of ethylene oxide for capping.

SUMMARY OF THE INVENTION

A method for preparing diols which contain essentially all primary hydroxyl groups without capping with ethylene oxide comprises reacting ethylene oxide, propylene oxide and/or butylene oxide with propylene glycol t-butyl ether or butylene glycol t-butyl ether or its aminated derivative then coupling these reaction products with organic diisocyanates or dibasic acids followed by cleavage of the t-butyl group with an acid catalyst.

DESCRIPTION OF THE PREFERRED EMBODIMENTS

The method of our invention is the manufacture of primary hydroxyl-containing glycols without capping with ethylene oxide. This can be accomplished by the use of the following known individual reactions by careful selection of starting materials and sequence.

REACTION SEQUENCE

Reactions 1 and 2
(Preparation of aminated derivatives of an alkyoxylated alkylene glycol t-butyl ether)

(1)

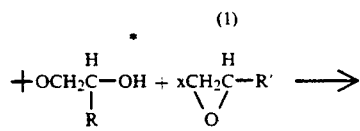

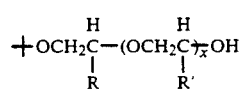

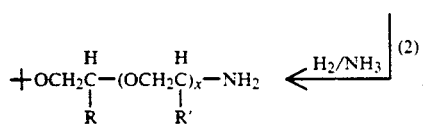

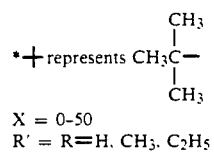

-continued

\*+ represents $CH_3\underset{\underset{CH_3}{|}}{\overset{\overset{CH_3}{|}}{C}}-$

X = 0-50
R' = R = H, CH$_3$, C$_2$H$_5$

Reaction 3
(Coupling of alkoxylated propylene glycol t-butyl ether or its aminated derivative with diisocyanate or dibasic acids)

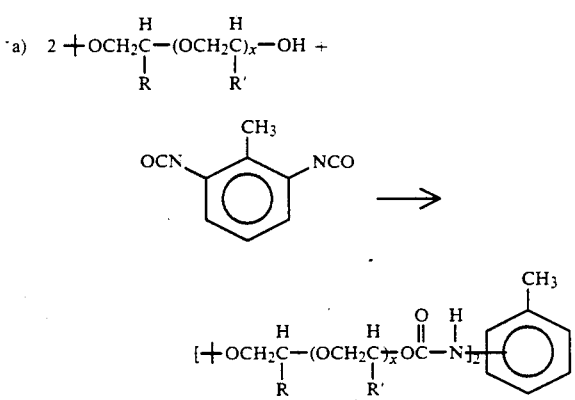

Reaction 4
(Removal or cleavage of t-butyl group to form diols)

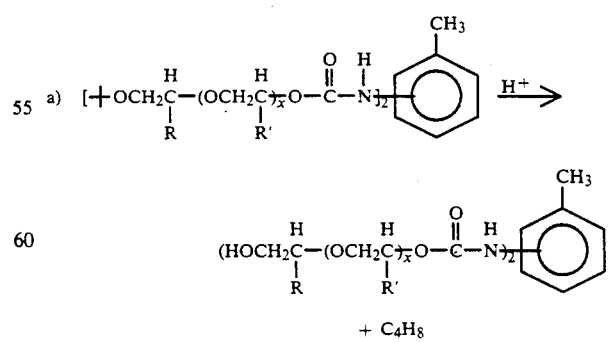

+ C$_4$H$_8$

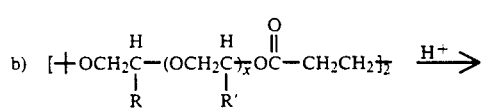

-continued

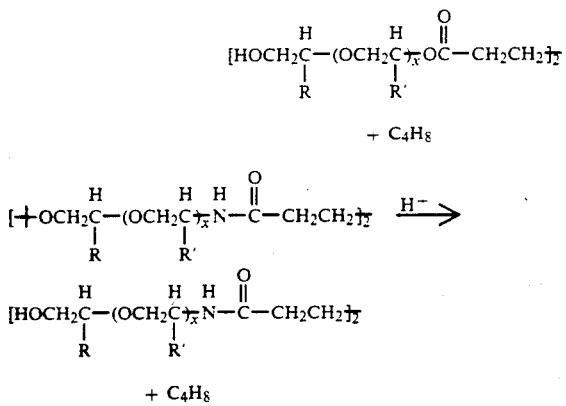

R = H, CH₃, C₂H₅
R' = H, CH₃, C₂H₅

The alkoxylation of a blocked alkylene glycol is shown as Reaction 1. Reaction 2 shows the preparation of aminated derivatives of the alkoxylated alkylene glycol t-butyl ethers. In order to obtain the primary hydroxyl group on the terminal carbon, the tertiary butyl (t-butyl) ether is preferred. The epoxide may be ethylene oxide, propylene oxide, or butylene oxide. Alkoxylation reactions are known in the art and are catalyzed by potassium or sodium hydroxides, for example. U.S. Pat. No. 3,535,307 describes typical alkoxylation techniques useful in this invention and is incorporated by reference. Other known methods for alkoxylation are acceptable for this invention. The degree of alkoxylation will determine the molecular weight of the product. The type of epoxide used will also help determine the solubility characteristics of the final material. It is known, for example, that ethylene oxide adducts are usually more water soluble than propylene oxide adducts an butylene oxide adducts. The desirable molecular weight will be determined by the amount of epoxide added in order to serve the purpose of the end user. Thus those skilled in the art will be able to adjust both water solubility and the molecular weight from the material in Reaction 1.

Reaction 2 is the amination of the alkoxylated material from Reaction 1. This amination of polyoxyalkylene alcohols is described in U.S. Pat. No. 3,654,370. This patent is incorporated by reference.

Reaction 3 shows the coupling of the alkoxylated propylene glycol t-butyl ether or its aminated derivative with diisocyanate or dibasic acids. In this general reaction, either the product of Reaction 1 which is hydroxyl terminated or the aminated derivative which is shown as the product of Reaction 2 may be coupled with any known diisocyanate or dibasic acid, for example. This coupling reaction enables the molecule to be further customized by providing an internal grouping to suit the purposes of the end user. Useful coupling agents are diisocyanates, blocked isocyanates, dibasic acids, dibasic acid esters, anhydrides, diepoxides, etc. This coupling reaction provides the symmetrical molecule containing two terminal t-butyl groups which may then be converted to the primary diols of this invention.

Reaction 4 shows the removal or cleavage of the t-butyl groups from the product of Reaction 3 to form the primary diols of this invention. The molecules from Reaction 3 are reacted with an acid. Those skilled in the art will be able to determine the proper conditions for cleavage to take place. Conditions may range from about room temperature to about 150° C., for example, and pressure low enough to allow the cleaved isobutylene to escape the reacting mixture. For example, atmospheric is acceptable but any pressure which achieves the results described is acceptable. As a result, the t-butyl end part of the molecule is cleaved and replaced by a primary hydroxyl group on each end. Thus the result of this reaction scheme is the manufacture of a variable molecular weight material which contains a primary hydroxyl group at each end. The acidic groups useful in the cleavage of Reaction 4 were found to be materials such as Amberlyst ® 15 ion-exchange resin and other acidic ion exchange resins, mineral acids, zeolites, etc.

The examples which follow show the preparation of compounds falling within the scope of our invention.

EXAMPLE 1

This example will illustrate the coupling of an 83.7 hydroxyl no. polyether, based on propylene glycol t-butyl ether (ARCOSOLV PTB, Arco Chemical Co.) with toluene diisocyanate (TDI). The polyether was made by reaction of ARCOSOLV PTB with four moles ethylene oxide and five moles propylene oxide.

Into a one-liter three-necked flask equipped with a stirrer, thermometer, nitrogen source, and water condenser were charged 500 g of the polyether and 0.04 g dibutyltin dilaurate. TDI (64.9 g) was then added to the flask. The reaction temperature rose from 25°-48° C. in one hour. The mixture was then heated to 97°-98° C. The finished product was a light-yellow viscous liquid which has the following properties:

| Viscosity, °F., cs | |
|---|---|
| 77 | 2316 |
| 100 | 894 |
| Mn | 1457 |
| Mw | 1593 |
| Dispersity | 1.093 |

All of EO was internal. The C¹³ NMR spectra of the product was consistent with the following structure:

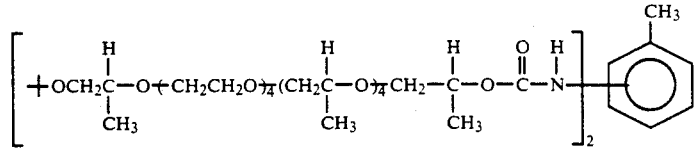

EXAMPLE 2

Into a one-liter three-necked flask equipped with a stirrer, thermometer, nitrogen source, and water condenser were charged 350 g of the polyether-TDI adduct of Example 1 and 70 g Amberlyst 15 acid ion-exchange resin. The reactants were then heated to 92° C., at which point gas evolution occurred. The reaction mixture was then heated at 95°–105° C. for 2.5 hours. Vigorous gas evolution occurred during that period. The product was then vacuum stripped and filtered. The finished product (256 g) was a light yellow viscous liquid which had the following properties:

| | |
|---|---|
| Acid no., mg KOH/g | 0.8 |
| Hydroxyl no., mg KOH/g | 89 |
| Water, wt % | 0.3 |
| Viscosity, °F., cs | |
| 77 | 2907 |
| 100 | 1070 |

EXAMPLE 3

This example will describe the condensation of the Arcosolv° PTB polyether of Example 1 with adipic acid.

Into a 250-ml three-necked flask equipped with a Dean-Stark trap, stirrer, thermometer, water condenser, and nitrogen source were charged 132 g of the 83.7 hydroxyl no. polyether and 14.6 g adipic acid. The reaction mixture was slowly heated to 220° C. and held at that temperature for four hours. Approximately 1.2 g water was collected in the overhead. The resultant product was a clear yellow semi-solid at room temperature. It had a hydroxyl no. of 0 indicating the absence of hydroxyl groups.

The NMR spectra of the material was in general agreement with the following structure:

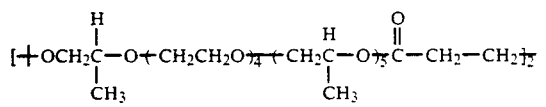

EXAMPLE 4

This example will illustrate the cleavage of the Arcosolv PTB polyether-adipic acid condensate of Example 3 to form the corresponding diol.

Into a 250 ml three-necked flask equipped with a stirrer, thermometer, water condenser, and nitrogen source were charged 114 g of the polyether-adipic acid condensate and 23 g Amberlyst 15 acid ion exchange resin. The reaction mixture was then heated at 95°–105° C. for four hours and was then vacuum stripped. The finished product was a dark yellow viscous liquid (80 g) which had a hydroxyl no. of 73.1. The $C^{13}$ NMR spectra was in general agreement with the following structure:

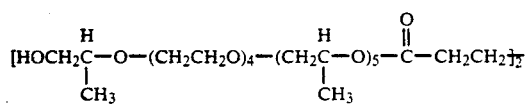

EXAMPLE 5

This example will show the condensation of the aminated Arcosolv PTB polyether and adipic acid. The aminated polyether (6180-60-3) had been prepared by the reductive amination of the polyether described in Example 1.

Into a 250 ml three-necked flask equipped with a stirrer, thermometer, Dean-Stark trap, water condenser, and nitrogen source were charged 113 g of the aminated polyether and 14.6 g adipic acid. The mixture was stirred at room temperature for fifteen minutes. The reaction mixture was then slowly heated to 220° C. and held there for three hours. Approximately 3.6 g water had been collected in the cold trap. The product was a light-yellow liquid which had the following properties:

| Sample no. | 6310-24 |
|---|---|
| Properties | |
| Total amine, meq/g | 0.09 |
| Hydroxyl no., mg KOH/g | 0.84 |

EXAMPLE 6

This example will describe the cleavage of the t-butyl group from the polyamide described in Example 5.

Into a 250 ml three-necked flask equipped with a stirrer, thermometer, water condenser and nitrogen source were charged 90 g of the polyamide and 18 g Amberlyst 15 acid ion exchange resin. The mixture was then heated at 95°–105° C. for four hours, vacuum stripped and filtered. The resultant product was a light-brown viscous liquid with a hydroxyl no. of 59.

EXAMPLE 7

A product prepared as in Example 2 was utilized in the preparation of flexible polyurethane foam as shown in the table below. As can be seen in each case, stable foam was prepared with good elongation.

| | Foam No. | | |
|---|---|---|---|
| | 6545-95A | 6545-95B | 6545-95C |
| Formulation, pbw | | | |
| THANOL ® F-3020[1] | 90 | 75 | 60 |
| Polyol of Example 2 | 10 | 25 | 40 |
| Water | 4.0 | 4.0 | 4.0 |
| L-711 Silicon[2] | 1.0 | 1.0 | 1.0 |
| THANCAT ® TD-33[3] | 0.3 | 0.3 | 0.3 |
| T-10 Catalyst[4] | 0.4 | 0.4 | 0.4 |
| Toluene diisocyanate | 50.2 | 50.8 | 51.5 |
| Isocyanate index | 1.05 | 1.05 | 1.05 |
| Details of Preparation | | | |
| Cream time, sec. | 12 | 15 | 18 |
| Rise time, sec. | 135 | 145 | 160 |
| Cure temperature, °C. (hr) | 90–100 (1) | 90–100 (1) | 90–100 (1) |
| Results | Stable foam good elongation | Stable foam good elongation | Stable foam good elongation |

[1]3000 m.w. triol; Arco Chemical Co.
[2]Union Carbide Chemical Co.
[3]33% Triethylenediamine in propylene glycol, Texaco Chemical Co.
[4]50% stannous octoate in dioctylphthalate; Witco Chemical Co.

What is claimed is:

1. A method for preparing diols which contain essentially all primary hydroxyl groups comprising reaction of ethylene oxide, propylene oxide and/or butylene oxide with ethylene, propylene or butylene glycol t-butyl ether, then coupling these reaction products with organic diisocyanates, dibasic acids, or dibasic esters followed by cleavage of the t-butyl group with an acid catalyst.

2. A method as in claim 1 wherein the coupling is done with organic diiosocyanates.

3. A method as in claim 1 wherein the coupling is done with dibasic acids.

4. A method for preparing diols which contain essentially all primary hydroxyl groups comprising reacting ethylene oxide, propylene oxide and/or butylene oxide with ethylene, propylene or butylene glycol t-butyl ether, then aminating this product and coupling these aminated reaction products with organic diisocyanates or dibasic acids followed by cleavage of the t-butyl group with an acid catalyst.

5. A method as in claim 4 wherein the coupling is done with organic diisocyanates.

6. A method as in claim 4 wherein the coupling is done with dibasic acids.

* * * * *